(12) United States Patent
Abbas et al.

(10) Patent No.: US 6,680,285 B2
(45) Date of Patent: Jan. 20, 2004

(54) SKIN CLEANSING BAR WITH HIGH LEVELS OF LIQUID EMOLLIENT

(75) Inventors: Syed Husain Abbas, Seymour, CT (US); Ray Hui, College Point, NY (US)

(73) Assignee: Unilever Home & Personal Care USA a division of Conopco, Inc., Greenwich, CT (US)

(*) Notice: Subject to any disclaimer, the term of this patent is extended or adjusted under 35 U.S.C. 154(b) by 144 days.

(21) Appl. No.: 10/006,094

(22) Filed: Dec. 3, 2001

(65) Prior Publication Data

US 2002/0137643 A1 Sep. 26, 2002

Related U.S. Application Data

(60) Provisional application No. 60/257,222, filed on Dec. 21, 2000.

(51) Int. Cl.[7] .................................................. A61K 7/50
(52) U.S. Cl. .................. 510/141; 510/151; 510/153; 510/156; 510/424; 510/428; 510/488
(58) Field of Search ............................... 510/130, 156, 510/424, 428, 488, 477, 141, 151, 153

(56) References Cited

U.S. PATENT DOCUMENTS

| | | | |
|---|---|---|---|
| 4,673,525 A | 6/1987 | Small et al. |
| 5,225,097 A | 7/1993 | Kacher et al. |
| 5,225,098 A | 7/1993 | Kacher et al. |
| 5,227,086 A | 7/1993 | Kacher et al. |
| 5,262,079 A | 11/1993 | Kacher et al. |

FOREIGN PATENT DOCUMENTS

| | | |
|---|---|---|
| JP | 703400 A | 7/1993 |
| WO | 98/27193 | 6/1998 |

*Primary Examiner*—Necholus Ogden
(74) *Attorney, Agent, or Firm*—Alan A. Bornstein

(57) ABSTRACT

A low water content cleansing composition in toilet bar form is described which includes high levels of emollients having a melting point below 25 C., 12-hydroxystearic acid as a structuring agent, and at least one detersive surfactant. Useful emollients that are liquid at room temperature may include triglycerides, petroleum oil, polyhydric alcohols and silicone oil, and are present in a concentration range of 5 to 60 wt. %. The inventive toilet bars have excellent mush and wear properties.

26 Claims, 2 Drawing Sheets

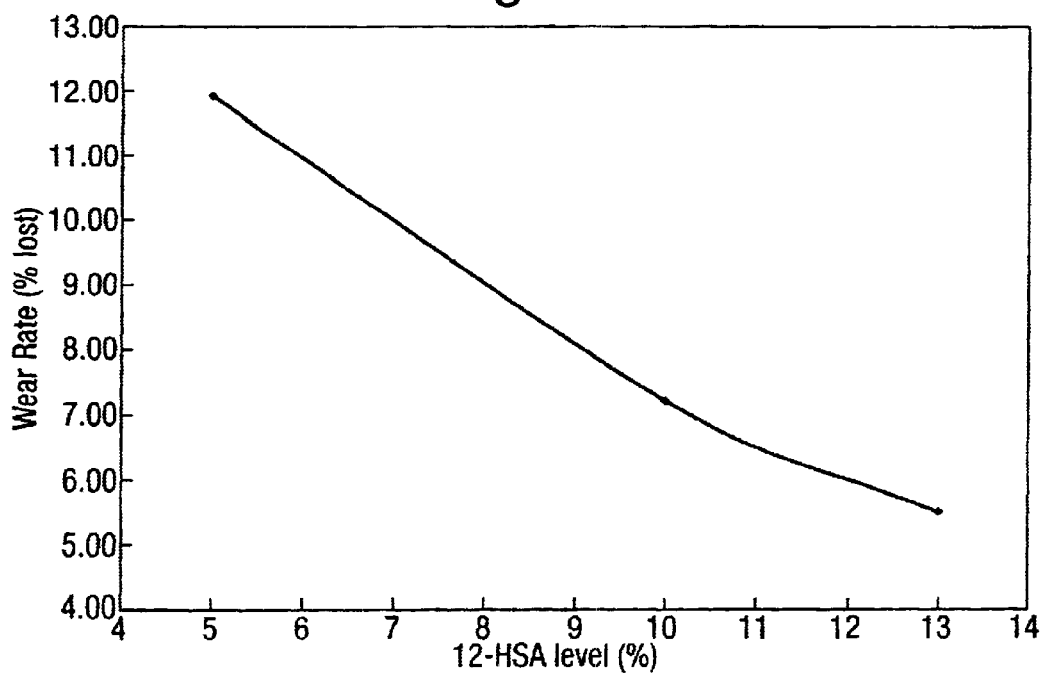

SKIN CLEANSING BAR WITH HIGH LEVELS OF LIQUID EMOLLIENT

This application claims priority to U.S. provisional application serial No. 60/257,222 filed Dec. 21, 2000.

BACKGROUND OF THE INVENTION

This invention relates generally to cleansing bars, and more particularly to cleansing bars having high levels of emollient.

Synthetic detergent or syndet toilet bars have found considerable use as mild cleansing bars but such bars have the potential to be soft and typically require structuring agents to be added to firm or harden the bar. Thus the main function of prior art structurants such as sodium stearate in syndet bars is to provide body and give structure to the product. For example, sodium stearate finds considerable use as a structurant or structuring agent in syndet bar formulations, forming a fibrous network structure which helps in improving the mush and rate of wear properties of the bars. However, there is a problem in structuring syndet bars containing high levels of emollients that are liquid at room temperature (25 C.).

12-Hydroxystearic acid has been previously employed as a strucuturing agent in high water content soap or syndet bars; see e.g. U.S. Pat. No. 5,225,097 issued to M. Kacher, et al. on Jul. 6, 1993 and U.S. Pat. No. 5,227,086 issued to M. Kacher, et al. on Jul. 13,1993; which are herein incorporated by reference. However the bars described by Kacher did not contain high levels of hydrophobic or hydrophilic emollients which have melting points below 25 C. J P Kokai publication no. 7034100A, issued to E. Yoshiyuki, et al. on Feb. 3,1995 describes a syndet bar containing 1 to 30% by weight of a liquid or semi-solid oil and 0.01 to 5% by weight of 12-hydroxystearic acid. However, the physical properties of the bars described by Yoshiyuki are not commercially acceptable, especially regarding the bar's wear rate and mush properties.

Unexpectedly the use of 12-hydroxystearic acid in syndet formulations at levels in excess of 5% by weight and with high levels of emollients that are liquid at room temperature (i.e. have a melting point below 25 C.) has been found to substantially improve the rate of wear and mush propensity of syndet toilet bars. High rates of wear and mush propensity are negative attributes of prior art syndet formulations as discussed above.

Furthermore it was unexpectedly discovered that the use of 12-hydroxy stearic acid in a low viscosity melt (Brookfield viscosity range of about 10 cps to about 40,000 cps) with high amounts of emollients which are liquid at room temperature gave a relatively stable melt, with no observable phase separation, between 70° C. and 110° C. with continuous mixing. In comparison, the same quantity of stearic acid as the sole structuring agent yields a very unstable syndet bar system where the hydrophobic emollient phase noticeably separates from the mix in the absence of phase stabilizers such as lauryl alcohol, or alternatively produces an undesirably soft bar in the absence of phase separation. It was also unexpectedly found that the use of 12-hydroxystearic acid in syndet formulations will improve the rate of wear and mush propensity of the formulations.

SUMMARY OF THE INVENTION

In one aspect, the present invention relates to a mild toilet bar with high levels of hydrophobic or hydrophilic emollients have a melting point below 25 C. and having 12-hydroxystearic acid as one of its structuring agents at a level above 5% by weight. Preferably, 12-hydroxystearic acid is the primary structuring agent present. Most preferably, 12-hydroxystearic acid is the sole structuring agent present.

Conventional structuring agents preferably are present in the inventive bar in the concentration range of about 5 to about 30% by weight. In the case where 12-hydroxystearic acid is the sole structuring agent, it is present in the concentration range of about 10 to 15%, preferably about 13 to 15% by weight.

In another aspect, the inventive toilet bar is mildly acidic to neutral having a pH range of about 5.0 to 7.0, preferably 5.0 to 6.0, and most preferably 5.3 to 5.7.

In a further aspect, the inventive toilet bar has a low moisture content, in the range of about 1 to less than about 15% by weight of water; preferably in the range of about 2 to about 13% by weight of water, and most preferably in the range of about 2 to about 6% by weight of water.

BRIEF DESCRIPTION OF THE DRAWINGS

FIG. 3 is a graph depicting the relationship of wear rate versus the concentration of 12-hydroxystearic acid (HSA) in the inventive toilet bar.

Figure 1:
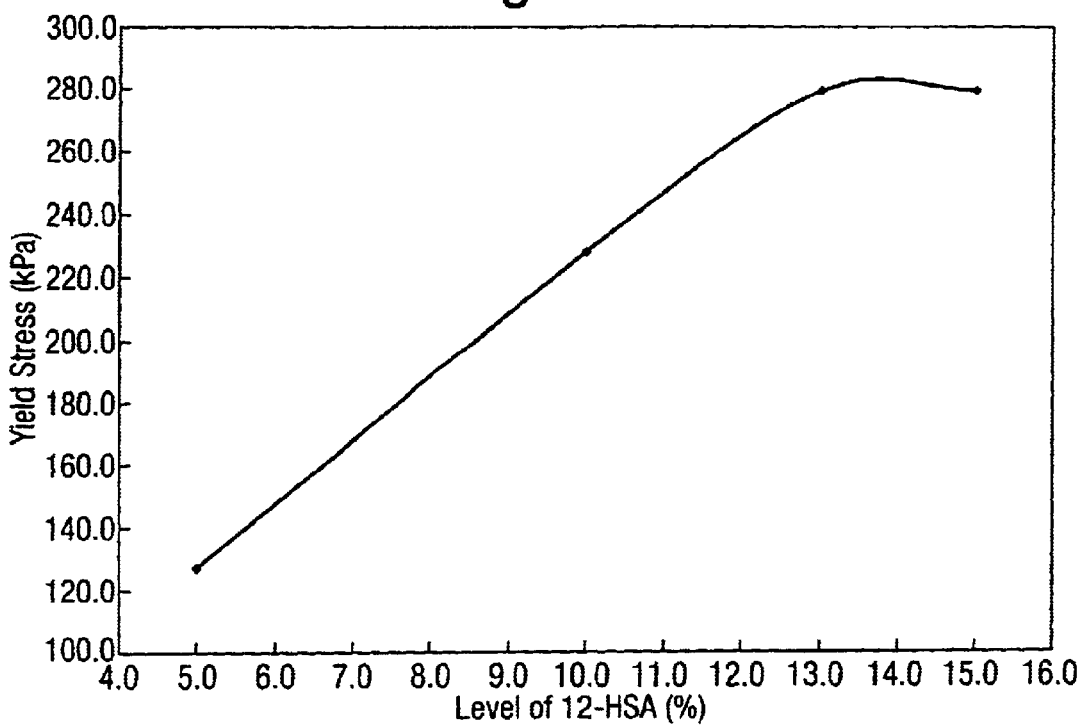
FIG. 1 is a graph depicting the relationship of yield stress versus the concentration of 12-hydroxystearic acid (HSA) in the inventive toilet bar.

DETAILED DESCRIPTION OF THE INVENTION:

In one aspect, the present invention relates to a mild toilet bar comprising:
  (i) about 5 to 60% by weight of a liquid emollient with a melting point below 25 C.;
  (ii) about 15% to 60% by weight of a surfactant; and
  (iii) more than about 5% by weight of 12-hydroxystearic acid, wherein the ratio of said 12-hydroxystearic acid to said liquid emollient is in the range of about 1 to 5 to about 10 to 1.

As used herein, the term liquid emollient refers to an emollient that is flowable at 25 C. prior to being blended in the cleansing composition. Similarly, the term solid emollient refers to an emollient that does not flow at 25 C. prior to being blended in the cleansing composition.

Preferably the inventive composition has a ratio of 12-hydroxystearic acid to liquid emollient in the range of about 1 to 5 to about 2 to 1. The liquid emollient is selected from hydrophillic and hydrophobic liquid emollients, and blends thereof. Preferably the liquid hydrophilic emollient is present in the concentration range of about 2 to 20% by weight, more preferably about 5 to 10% by weight. Preferably the liquid hydrophobic emollient is present in the concentration range of about 2 to 45% by weight, more preferably about 10 to 30% by weight. Useful hydrophilic liquid emollients are selected from polyhydric alcohols, polyols, saccharides, and mixtures thereof. Useful hydrophobic liquid emollients are selected from triglycerides, hydrocarbons, silicones, fatty acids, fatty, esters, fatty alcohols, and blends thereof.

The inventive composition preferably contains 12-hydroxystearic acid in the range of about 5 to 20% by weight, more preferably about 10 to about 15% by weight.

The inventive composition preferably includes at least one acyl isethionate, preferably in the concentration range of about 5 to about 45% by weight of total acyl isethionates. Most preferably at least one of the acyl isethionates is sodium cocoyl isethionate.

The inventive composition further comprises a solid emollient. Useful solid emollients are selected from the group of fatty acids, fatty esters, fatty alcohols, waxes, or triglycerides. Preferably the solid emollient and liquid emollient is in the ratio range of about 1 to 10 to about 10 to 1, more preferably in the range of about 1 to 5 to about 1 to 2.

In another aspect of the invention a toilet bar composition is provided comprising:
(i) about 5 to 60% by weight of a liquid emollient with a melting point below 25 C.;
(ii) about 15% to 60% by weight of a surfactant;
(iii) more than about 5% by weight of 12-hydroxystearic acid, wherein the ratio of said 12-hydroxystearic acid to said emollient is in the range of about 1 to 5 to about 10 to 1; and
(iv) less than about 15% by weight of water.

Preferably the ratio of 12-hydroxystearic acid to liquid emollient is in the range of about 1 to 5 to about 1 to 3. Preferably the bar contains less than about 6% by weight of water.

In a further aspect of the invention, a toilet bar composition is provided comprising:
a) about 5 to 60% by weight of a liquid emollient with a melting point below 25 C.;
b) about 15% to 60% by weight of a surfactant;
c) more than about 5% by weight of 12-hydroxystearic acid, wherein the ratio of said 12-hydroxystearic acid to said liquid emollient is in the range of about 1 to 5 to about 10 to 1; and
d) a hydrophilic emollient, and a hydrophobic emollient; wherein the ratio of said hydrophilic emollient and said hydrophobic emollient is in the range of about 1 to 10 to about 5 to 1.

The inventive toilet bar composition preferably has a ratio of hydrophilic emollients to hydrophobic emollients in the range of about 1 to 8 to about 1 to 5.

In a further aspect of the invention, a toilet bar composition is provided comprising:
a) about 10 to 30% by weight of a triglyceride liquid emollient with an iodine value in the range of 80 to 140 and a melting point below 25 C.;
b) about 15 to 60% by weight of an acyl isethionate;
c) about 10 to 15% by weight of 12-hydroxystearic acid; and less than about 6% water.

In still a further aspect of the invention, a toilet bar composition is provided comprising:
a) about 5 to 60% by weight of a hydrophobic liquid emollient with a melting point below 25 C.;
b) about 15% to 60% by weight of a surfactant;
c) more than about 5% by weight of 12-hydroxystearic acid, and wherein the ratio of said surfactant to said hydrophobic liquid emollient is less than about 5 to 3.

Preferably the ratio of surfactant to hydrophobic liquid emollient is in the range of about 10 to 1 to about 1 to 3, more preferably in the range of about 4 to 3 to about 1 to 2.

Preferably, 12-hydroxystearic acid is the primary structuring agent present in the inventive bar. Most preferably, 12-hydroxystearic acid is the sole structuring agent present. Conventional structuring agents preferably are present in the inventive bar in the concentration range of about 5 to about 30% by weight. In the case where 12-hydroxystearic acid is the sole structuring agent, it is present in the concentration range of about 10 to 15%, preferably about 13 to 15% by weight.

In another aspect, the inventive toilet bar is mildly acidic to neutral having a pH range of about 5.0 to 7.0, preferably 5.0 to 6.0, and most preferably 5.3 to 5.7.

In a further aspect, the inventive toilet bar has a low moisture content, in the range of about 1 to less than about 15% by weight of water; preferably in the range of about 2 to about 13% by weight of water, and most preferably in the range of about 2 to about 6% by weight of water.

Surfactants:

Surfactants are an essential component of the invenvtive toilet bar. They are compounds that have hydrophobic and hydrophilic portions that act to reduce the surface tension of the aqueous solutions they are dissolved in. Useful surfactants can include anionic, nonionic, amphoteric, and cationic surfactants, and blends thereof.

Anionic Surfactants:

The toilet bar of the present invention contains one or more anionic detergents. The anionic detergent active which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glucosides and acyl isethionates, and the like.

Sulfosuccinates may be monoalkyl sulfosuccinates having the formula:

$$R^4O_2CCH_2CH(SO_3M)CO_2M; \text{ and}$$

amide-MEA sulfosuccinates of the formula;

$$R^4CONHCH_2CH_2O_2CCH_2CH(SO_3M)CO_2M$$

wherein $R^4$ ranges from $C_8$–$C_{22}$ alkyl and M is a solubilizing cation.

Sarcosinates are generally indicated by the formula:

$$R^1CON(CH_3)CH_2CO_2M,$$

wherein $R^1$ ranges from $C_8$–$C_{20}$ alkyl and M is a solubilizing cation.

Taurates are generally identified by formula:

$$R^2CONR^3CH_2CH_2SO_3M$$

wherein $R^2$ ranges from $C_8$–$C_{20}$ alkyl, $R^3$ ranges from $C_1$–$C_4$ alkyl and M is a solubilizing cation.

The inventive bar contains anionic surfactants, preferably contains $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Total surfactants will generally range from about 15% to about 60% by weight of the toilet bar. Preferably, this component is present from about 25% to about 40% in the bar.

The acyl isethionate may be an alkoxylated isethionate such as is described in Ilardi et al., U.S. Pat. No. 5,393,466, titled "Fatty Acid Esters of Polyalkoxylated isethonic acid; issued Feb. 28, 1995; hereby incorporated by reference. This compound has the general formula:

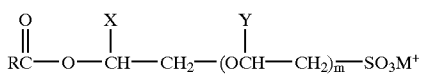

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

It should be understood that the bar may comprise a certain amount of soap as anionic surfactant. When used, the term "soap" is used in its popular sense, i.e., alkalimetal or alkanol ammonium salt of aliphatic alkane or alkene monocarboxylic acids. Sodium, potassium, mono-, di- and triethanol ammonium cations, or combinations thereof, are suitable for purposes of the invention. Generally, sodium soaps are used. Soaps useful herein are the well known alkali metal salts of natural or synthetic aliphatic (alkanoic or alkenoic) acids having 13 to 22 cations, preferably 12 to 18. They may be described as alkali metal carboxylates of acrylic hydrocarbons having about 12 to 22 carbons.

Anionic surfactants with Krafft points of up to 40 to 45 C can be used in the formulation. Anionic surfactants with a Krafft point below room temperature are preferred.

Amphoteric Surfactants

One or more amphoteric surfactants may be used in this invention. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

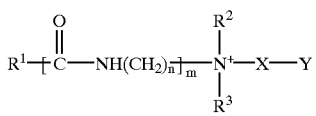

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is —$CO_2$— or —$SO_3$—

Suitable amphoteric surfactants within the above general formula include simple betaines of formula:

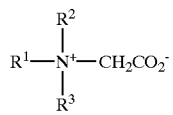

and amido betaines of formula:

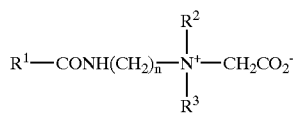

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

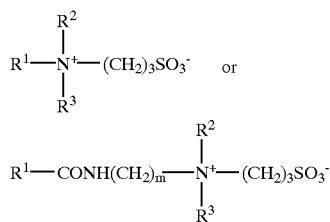

where m is 2 or 3, or variants of these in which —$(CH_2)_3$ $SO_3$— is replaced by

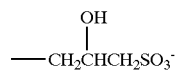

In these formulae $R^1$, $R^2$ and $R^3$ are as discussed previously.

Nonionic Surfactants

One or more nonionic surfactants may also be used in the toilet bar of the present invention.

The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$–$C_{22}$) phenols ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

The nonionic may also be a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995;

which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

Cationic Surfactants

One or more cationic surfactants may also be used in the inventive toilet bar.

Examples of cationic detergents are the quaternary ammonium compounds such as alkyldimethylammonium halogenides.

Other suitable surfactants which may be used are described in U.S. Pat. No. 3,723,325 to Parran Jr. titled "Detergent Compositions Containing Particle Deposition Enhancing Agents" issued Mar., 27, 1973; and "Surface Active Agents and Detergents" (Vol. I & II) by Schwartz, Perry & Berch, both of which are also incorporated into the subject application by reference.

Structuring Agents

The inventive toilet bar also contains 5 to 30% by wt., preferably 10 to 15% by wt. of total structurant including 12-hydroxystearic acid. Preferably the only structurant in the toilet bar is 12-hydroxystearic acid and is present at 10 to 15% by wt., preferably at 11 to 15% by wt., and most preferably at 13 to 15% by wt. Structurants are used to enhance the bar integrity, improve the processing properties, and enhance desired user sensory profiles. Suitable co-structurants are generally long chain, preferably straight and saturated, ($C_8$–$C_{24}$) fatty acid or ester derivative thereof; and/or branched long chain, preferably straight and saturated, ($C_8$–$C_{24}$) alcohol or ether derivatives thereof. These co-structurants are preferably present at a level which allows the pH of the bar to remain in the 5.5 to 6.0 range. The pH of the formulation may be adjusted by incoprorating sodium or potassium salts of fatty acids. However, it is preferred not to neutralize 12-hydroxysteric acid when it is used as the sole structuring agent.

The inventive bar also optionally contains fillers selected from inorganic minerals such as calcium sulfate, and the like; and starches, preferably water soluble starches such as maltodextrin and the like and polyethylene wax or paraffin wax, and the like. Fillers may be present in the inventive toilet bar in the range of 1 to 15% by weight, preferably 1 to 5% by weight.

Other co-structuring aids can also be selected from water soluble polymers chemically modified with a hydrophobic moiety or moieties, for example, EO-PO block copolymer, hydrophobically modified PEGs such as POE(200)-glyceryl-stearate, glucam DOE 120 (PEG 120 Methyl Glucose Dioleate), and Hodag CSA-102 (PEG-150 stearate), and Rewoderm® (PEG modified glyceryl cocoate, palmate or tallowate) from Rewo Chemicals.

Other co-structuring aids which may be used include Amerchol Polymer HM 1500 (Nonoxynyl Hydroethyl Cellulose).

In addition, the inventive bar composition of the invention may include 0 to 15% by wt. optional ingredients as follows:
perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer) and the like; all of which are useful in enhancing the appearance or cosmetic properties of the product.

The compositions may further comprise antimicrobials such as 2-hydroxy-4,2', 4' trichlorodiphenylether (DP300); preservatives such as dimethyloldimethylhydantoin (Glydant XL1000), parabens, sorbic acid etc., and the like.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and the like may be used advantageously in amounts of about 0.01% or higher if appropriate.

Cationic polymers as conditioners which may be used include Quatrisoft LM-200 Polyquaternium-24, Merquat Plus 3330-Polyquaternium 39; and Jaguar® type conditioners.

Polyethylene glycols as conditioners which may be used include:

| | |
|---|---|
| Polyox WSR-205 | PEG 14 M, |
| Polyox WSR-N-60K | PEG 45 M, or |
| Polyox WSR-N-750 | PEG 7 M. |

Another ingredient which may be included are exfoliants such as polyoxyethylene beads, walnut shells and apricot seeds, and the like.

Compositions of the inventive toilet bar also comprise 1% to 13% by wt., preferably 2% to 6% by wt. water.

In one embodiment of the invention, the inventive toilet bar's composition comprises no more than about 60% surfactant and preferably in the range of 20 to 60% by weight.

The emollient "composition" may be a single benefit agent component or it may be a benefit agent compound added via a carrier. Further the benefit agent composition may be a mixture of two or more compounds one or all of which may have a beneficial aspect. In addition, the benefit agent itself may act as a carrier for other components one may wish to add to the bar composition.

The benefit agent can be either a hydrophobic or hydrophilic emollient or a blend thereof. Preferably one or more hydrophobic emollients are used either alone, or together with one or more hydrophilic emollients. Most preferably, hydrophobic emollients are used in excess of hydrophilic emollients in the inventive bar. Hydrophobic emollients are preferably present in the concentration range of about 5 to 45% by weight, preferably 10 to 25% by weight. Hydrophillic emollients may preferably be present in the concentration range of 5 to 20% by weight. The term "emollient" is defined as a substance which softens or improves the elasticity, appearance, and youthfulness of the skin (stratum corneum) by either increasing its water content, adding, or replacing lipids and other skin nutrients; or both, and keeps it soft by retarding the decrease of its water content. Emollients which are either solid or liquid at 25 C. may be used individually or as a blend of emollients with melting points above and below 25 C. These emollients are present in the concentration range of about 5 to 60% by weight. It is preferred that at least one emollient has a melting point below 25 C. Preferably the total low melting emollients are present in the concentration range of about 20 to 35% by weight and is hydrophobic.

Useful emollients include the following:
  (a) silicone oils and modifications thereof such as linear and cyclic polydimethylsiloxanes; amino, alkyl, alkylaryl, and aryl silicone oils;
  (b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin, and derivatives thereof;

(d) hydrophobic plant extracts;

(e) hydrocarbons such as liquid paraffins, vaseline, microcrystalline wax, ceresin, squalene, pristan and mineral oil;

(f) higher fatty acids such as lauric, myristic, palmitic, stearic, behenic, oleic, linoleic, linolenic, lanolic, isostearic, arachidonic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils;

(j) lipids such as cholesterol, ceramides, sucrose esters and pseudo-ceramides as described in European Patent Specification No. 556,957;

(k) vitamins, minerals, and skin nutrients such as vitamins A, E, and K; vitamin alkyl esters, including vitamin C alkyl esters; magnesium, calcium, and milk.

(l) sunscreens such as octyl methoxyl cinnamate (Parsol MCX) and butyl methoxy benzoylmethane (Parsol 1789);

(l) phospholipids;

(m) polyhydric alcohols such as glycerine and propylene glycol; and polyols such as polyethylene glycols, (n) antiaging compounds such as alpha hydroxy acids, beta hydroxy acids; and (o) mixtures of any of the foregoing components, and the like.

Preferred emollient benefit agents are selected from triglyceride oils, petroleum oils, polyhydric alcohols and silicone oils. More preferably sunflower seed oil, propylene glycol and glycerin are used. Further preferred emollients are triglycerides having an iodine value from about 50 to about 145, with a range of about 80 to about 130 being especially preferred.

The composition may also comprise decorative or functional particulates including speckles, coloured or reflective particles, or shaped particles, encapsulated beads, sponge, and the like.

Conventional art recognised melt cast processing techniques may be used to fabricate the inventive toilet bar. For example, the melted components of the inventive bar are usually blended together at elevated temperatures. Optionally the water level may be adjusted and the blending will continue. Next an optional drying step may follow whereby the water is reduced. Preferably the water level of the ingredients is selected to be low enough to avoid the drying process. Finally, the molten cleansing composition is poured into molds and cooled to its hardening point. The molds may be made of any rigid material that is not subject to attack by the ingredients of the toilet bar. Mold materials may include plastic, metal, glass, ceramic, composite, or elastomeric materials and the like. Cooling the molten cleansing materials can be accomplished by art recognised cooling techniques including refrigeration, cryogenics, ambient air and the like. Controlled cooling using thermostatic control cooling devices may also be employed.

Conventional art recognised packaging materials may be used to package the inventive toilet bar. The package may hold one or more separately packaged bars. The package may also have an optional transparent area to view part or all of the bar contained therein. Paper, plastic, or coated paper, or other flexible or rigid packaging materials that are compatible with the toilet bar may be used. Single layer or laminated packaging material structures may also be used. Preferably, the packaging material is moisture proof, and mold resistant. The packaging material should have good barrier properties to prevent the loss of volatile cleansing composition ingredients such as perfume. Examples, of useful barrier materials are polymer coated paper board or other appropriate materials. Hot melt adhesive or contact adhesive such as glue may be used to adhere a portion of the carton and the wrapper. An appropriate coating would be a low density polyethylene coating and the like.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated. Physical test methods are described below:

Formulation and Melt Casting Details

All the ingredients except for sodium cocoyl isethionate, perfume, and triglycerides, are melted at 100 to 105 C and dissolved. Then sodium cocoyl isethionate is added slowly and dissolved by continuous mixing. Next the triglyceride(s) is added to the homogeneous mass. The mass is then allowed to cool to 70 to 90 C. at which time the perfume is added. Next the mass is then poured into molds and allowed to cool to 25 C. under ambient conditions.

EXAMPLE 1

Syndet toilet bars with and without lauryl alcohol as a phase stabilizer were melt cast from the formulations listed in table 1. Bars A and B are comparative using stearic acid as the structuring agent. Bars C and D represent embodiments of the present invention using 12-hydroxystearic acid as the structuring agent. The bars were compared for melt phase stability, hardness, and mush using the test methods described below. Comparative bar A did not yield a homogeneous bar due to phase separation. Comparative bar B containing lauryl alcohol as a phase stabilizer yielded a homogeneous bar but was considerably softer than inventive bar D which contained the same amount of lauryl alcohol. Concentrations are given in parts.

TABLE 1

| Ingredients | A | B | C | D |
|---|---|---|---|---|
| Sodium cocoyl isethionate, f | 25.00 | 25.00 | 25.00 | 25.00 |
| Alfa Olefin Sulfonate, f | 9.00 | 9.00 | 9.00 | 9.00 |
| Sodium Lauryl Ether Sulfate (2 EO), f | 9.00 | 9.00 | 9.00 | 9.00 |
| Propylene Glycol, a,c | 7.00 | 7.00 | 7.00 | 7.00 |
| Glycerin, a,c | 7.00 | 7.00 | 7.00 | 7.00 |
| 12-hydroxystearic acid | — | — | 14.00 | 14.00 |
| stearic acid (99%), b,d | 14.00 | 14.00 | — | — |
| Sunflower Seed Oil a,d,e | 25.00 | 25.00 | 25.00 | 25.00 |
| Water | 4.00 | 4.00 | 4.00 | 4.00 |
| Lauryl Alcohol, a,c | — | 10.00 | — | 10.00 |
| Total | 100.00 | 110.00 | 100.00 | 110.00 |
| Bar hardness (KPa) | — | 50 | 186 | 186 |
| Rate of Wear | 28.1 | 25.0 | 12.3 | 10.9 |
| % Mush | 39.8 | 28.1 | 34.7 | 24.7 | a: liquid emollient
b: solid emollient
c: hydrophillic liquid emollient
d. hydrophobic liquid emollient
e. triglyceride liquid emollient with an iodine value of 80–140
f. surfactant

EXAMPLE 2

The effect of replacing stearic acid (bar F) with 12-hydroxystearic acid (bar E) was seen to improve bar hardness as illustrated in table 2.

TABLE 2

| Ingredients | E Inventive | F Comparative |
|---|---|---|
| Sodium Cocoyl Isethionate, f | 22.35 | 22.35 |
| Stearic acid/ Palmitic Acid, b,d | 5.88 | 5.88 |
| Coco Fatty acid, b,d | 0.59 | 0.59 |
| Sodium Isethionate, f | 0.50 | 0.50 |
| Alfa Olefin Sulfonate, f | 7.23 | 7.23 |
| Sodium Lauryl Ether Sulfate (2 EO), f | 7.23 | 7.23 |
| Perfume | 1.25 | 1.25 |
| Titanium Dioxide | 1.00 | 1.00 |
| Propylene Glycol, a,c | 5.00 | 5.00 |
| Glycerin, a,c | 4.00 | 4.00 |
| Lauryl Alcohol, a,d | 4.97 | 4.97 |
| 12-hydroxystearic acid | 11.00 | — |
| stearic acid | — | 11.00 |
| Sunflower Seed Oil, a,d,e | 25.00 | 25.00 |
| Water | 4.00 | 4.00 |
|  | 100.00 | 100.00 |
| Bar hardness | 0.20 MPa | 0.116 MPa |
| Rate of Wear | 12.39% | 19.05% | a: liquid emollient
b: solid emollient
c: hydrophillic liquid emollient
d. hydrophobic liquid emollient
e. triglyceride liquid emollient with an iodine value of 80–140
f. surfactant

EXAMPLE 3

Figure 2:
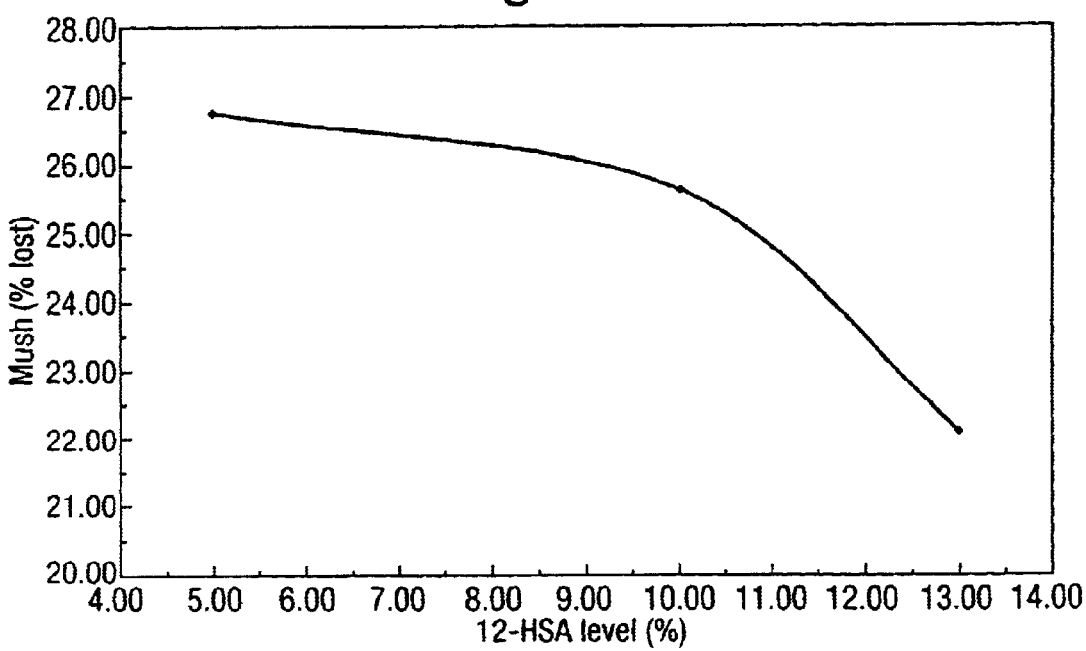
FIG. 2 is a graph depicting the relationship of mush versus the concentration of 12-hydroxystearic acid (HSA) in the inventive toilet bar.

The effect of increasing the level of 12-hydroxystearic acid in the inventive toilet bar was shown to improve mush properties, hardness, and to reduce the rate of wear as shown in table 3 and FIGS. 1–3. Lather measurement of the different formulations indicates that there is no significant difference between the three formulations for lather.

TABLE 3

| Ingredients | G | H | I | J |
|---|---|---|---|---|
| Sodium Cocoyl Isethionate, f | 28.22 | 25.66 | 24.10 | 23.00 |
| Stearic acid/ Palmitic Acid, b,d | 7.42 | 6.75 | 6.34 | 6.05 |
| Coco Fatty acid, b,d | 0.75 | 0.68 | 0.64 | 0.61 |
| Sodium Isethionate, f | 0.63 | 0.57 | 0.53 | 0.51 |
| Alfa Olefin Sulfonate, f | 8.99 | 8.17 | 7.70 | 7.40 |
| Sodium Lauryl Ether Sulfate (2 EO), f | 8.99 | 8.17 | 7.7 | 7.40 |
| Perfume | 1.00 | 1.00 | 1.00 | 1.00 |
| Titanium Dioxide | 1.00 | 1.00 | 1.00 | 1.00 |
| Propylene Glycol, a,c | 5.00 | 5.00 | 5.00 | 5.00 |
| Glycerin. a,c | 4.00 | 4.00 | 4.00 | 4.00 |
| Lauryl Alcohol, a,d | 5.00 | 5.00 | 5.00 | 5.00 |
| 12-hydroxystearic acid | 5.00 | 10.00 | 13.00 | 15.00 |
| Sunflower Seed Oil, a,d,e | 20.00 | 20.00 | 20.00 | 20.00 |
| Water | 4.00 | 4.00 | 4.00 | 4.00 |
| Bar Hardness (25° C.) kPa | 127 | 228 | 279 | 279 |
| Rate of Wear for 10 washes (%) | 11.92 | 7.22 | 5.51 | — |
| Mush (%) | 26.77 | 25.63 | 22.11 | — | a: liquid emollient
b: solid emollient
c: hydrophillic liquid emollient
d. hydrophobic liquid emollient
e. triglyceride liquid emollient with an iodine value of 80–140
f. surfactant Description of Test Methods:
Evaluation of Mush:

Immerse a weighed toilet bar in 250 ml water (at 25 C.), in a beaker for four hours. Scrape the mush from the bar with a soft plastic knife. Weigh the scraped bar after allowing to dry at room temperature 24 hours. The weight change multiplied by 100 and divided by the initial weight of the bar denotes the mush of the bar. Mush is calculated as the average of three bars.

Rate of Wear:

Wet a pre-weighed bar in running water and rotate 15 times while in the tester's hand. Place on a support stand. Repeat 10 times at half hour intervals. Weigh the washed bar after allowing to dry at room temperature for 16 hours. The weight change multiplied by 100 and divided by the initial weight of the bar denotes the rate of wear of the bar.

Foam (Lather) Measurement:

A tester rotates a wet bar ten times between his hands. Then 5 mls of 95 C water is added and the bar is rubbed with the hands to generate lather. Then the tester dips his hands in a water tank under an inverted funnel coupled to a measuring cylinder so as to collect and measure the volume in mls of the generated lather.

Bar Hardness Measurement:

The method used for the hardness measurement is sectilometry or cutting the soap with a suitable wire as described e.g. by Bowen and Thomas in *Trans. Farad. Soc.* 31, 164, (1935).

EXAMPLE 4

A syndet toilet bar "J" containing 40% by weight of sunflower seed oil was melt cast from the formulation listed in table 4 and a homogeneous bar was obtained with acceptable rate of wear and mush properties.

| Ingredients | % |
|---|---|
| Sodium Cocoyl Isethionate | 26.00 |
| Stearic acid/ Palmitic Acid | 6.83 |
| Coco Fatty acid | 0.69 |
| Sodium Isethionate | 0.58 |

-continued

| Ingredients | % |
| --- | --- |
| Propylene Glycol | 3.00 |
| Glycerin | 2.00 |
| Lauryl Alcohol | 2.00 |
| 12-hydroxystearic acid | 14.90 |
| Sunflower Seed Oil | 40.00 |
| Water | 4.00 |
| Total | 100.00 |

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

What is claimed is:

1. A toilet bar composition comprising:
   (i) about 5 to 60% by weight of a liquid emollient with a melting point below 25 C.;
   (ii) about 15% to 60% by weight of a surfactant;
   (iii) more than about 5% by weight of 12-hydroxystearic acid, wherein the ratio of said 12-hydroxystearic acid to said emollient is in the range of about 1 to 5 to about 10 to 1; and
   (iv) less than about 15% by weight of water.

2. The composition of claim 1 wherein the ratio of said 12-hydroxystearic acid to said emollient is in the range of about 1 to 5 to about 1 to 3.

3. The composition of claim 1 wherein the bar contains less than about 6% by weight of water.

4. A toilet bar composition comprising:
   a) about 5 to 60% by weight of a liquid emollient with a melting point below 25 C.;
   b) about 15% to 60% by weight of a surfactant;
   c) more than about 5% by weight of 12-hydroxystearic acid, wherein the ratio of said 12-hydroxystearic acid to said liquid emollient is in the range of about 1 to 5 to about 10 to 1;
   d) a hydrophilic emollient, and a hydrophobic emollient; wherein the ratio of said hydrophilic emollient and said hydrophobic emollient is in the range of about 1 to 10 about 5 to 1, and
   e) less than about 15% by wt. of water.

5. The toilet bar composition of claim 4 wherein the ratio of said hydrophilic emollient to said hydrophobic emollient is in the range of about 1 to 8 to about 1 to 5.

6. A toilet bar composition comprising:
   about 10 to 30% by weight of a triglyceride liquid emollient with an iodine value in the range of 80 to 140 and a melting point below 25 C.;
   about 15 to 60% by weight of an acyl isethionate;
   about 10 to 15% by weight of 12-hydroxystearic acid; and
   less than about 6% water.

7. A toilet bar composition comprising:
   a) about 5 to 60% by weight of a hydrophobic liquid emollient with a melting point below 25 C.;
   b) about 15% to 60% by weight of a surfactant;
   c) more than about 5% by weight of 12-hydroxystearic acid, and wherein the ratio of said surfactant to said hydrophobic liquid emollient is less than about 5 to 3.
   d) less than about 15% by wt. of water.

8. The toilet bar composition of claim 7 wherein the ratio of said surfactant to said hydrophobic liquid emollient is in the range of about 10 to 1 to about 1 to 3.

9. The toilet bar composition of claim 7 wherein the ratio of said surfactant to said hydrophobic liquid emollient is in the range of about 4 to 3 to about 1 to 2.

10. The composition of claim 1 wherein the ratio of said 12-hydroxystearic acid to said liquid emollient is in the range of about 1 to 5 to about 2 to 1.

11. The composition of claim 1 wherein said liquid emollient is selected from hydrophillic and hydrophobic liquid emollients, and blends thereof.

12. The composition of claim 11 wherein said liquid hydrophilic emollient is present in the concentration range of about 2 to 20% by weight.

13. The composition of claim 11 wherein said liquid hydrophilic emollient is present in the concentration range of about 5 to 10% by weight.

14. The composition of claim 11 wherein said liquid hydrophobic emollient is present in the concentration range of about 2 to 45% by weight.

15. The composition of claim 11 wherein the hydrophobic liquid emollient is present in the concentration range of about 10 to 30% by weight.

16. The composition of claim 11 wherein said hydrophilic liquid emollient selected from polyhydric alcohols, polyols, saccharides, and mixtures thereof.

17. The composition of claim 11 wherein said hydrophobic liquid emollient is selected from triglycerides, hydrocarbons, silicones, fatty acids, fatty esters, fatty alcohols, and blends thereof.

18. The composition of claim 1 wherein said concentration of 12-hydroxystearic acid is in the range of about 5 to 20% by weight.

19. The composition of claim 18 wherein said concentration of 12-hydroxystearic acid is more than about 10 to about 15% by weight.

20. The composition of claim 1 wherein said surfactant includes at least one acyl isethionate.

21. The composition of claim 20 wherein said at least one acyl isethionates are collectively in the concentration range of about 5 to about 45% by weight.

22. The composition of claim 20 wherein said at least one acyl isethionates includes sodium cocoyl isethionate.

23. The composition of claim 1 further comprising a solid emollient which is solid at 25 C.

24. The composition of claim 23 wherein said solid emollient is selected from the group of fatty acids, fatty esters, fatty alcohols, waxes, or triglycerides.

25. The composition of claim 23 wherein said solid emollient and said liquid emollient is in the ratio of about 1 to 10 to about 10 to 1.

26. The composition of claim 25 wherein said solid emollient and said liquid emollient is in the ratio of about 1 to 5 to about 1 to 2.

* * * * *